(12) United States Patent
Harms et al.

(10) Patent No.: US 9,474,861 B2
(45) Date of Patent: Oct. 25, 2016

(54) DRUG DELIVERY DEVICE BODY

(75) Inventors: Michael Harms, Frankfurt am Main (DE); Steffen Raab, Frankfurt am Main (DE); Uwe Dasbach, Frankfurt am Main (DE); Udo Stauder, Frankfurt am Main (DE)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 13 days.

(21) Appl. No.: 13/258,155

(22) PCT Filed: Mar. 31, 2010

(86) PCT No.: PCT/EP2010/054341
§ 371 (c)(1),
(2), (4) Date: Dec. 6, 2011

(87) PCT Pub. No.: WO2010/112560
PCT Pub. Date: Oct. 7, 2010

(65) Prior Publication Data
US 2012/0078195 A1    Mar. 29, 2012

Related U.S. Application Data

(60) Provisional application No. 61/169,846, filed on Apr. 16, 2009.

(30) Foreign Application Priority Data

Mar. 31, 2009   (EP) ..................................... 09004664

(51) Int. Cl.
*A61M 5/31* (2006.01)
*A61M 5/315* (2006.01)

(52) U.S. Cl.
CPC .......... *A61M 5/3129* (2013.01); *A61M 5/3155* (2013.01); *A61M 2005/3125* (2013.01); *A61M 2205/6063* (2013.01)

(58) Field of Classification Search
CPC ........... A61M 5/3129; A61M 5/3155; A61M 2005/3125; A61M 2205/6063
USPC .................................................. 604/181, 189
See application file for complete search history.

(56) References Cited

U.S. PATENT DOCUMENTS 3,288,318 A * 11/1966 Corbin et al. ................ 215/365
3,885,562 A    5/1975 Lampkin (Continued)

FOREIGN PATENT DOCUMENTS

| EP | 0615762 | 9/1994 |
| EP | 1923083 | 5/2008 |
| WO | 2008/091838 | 7/2008 |

OTHER PUBLICATIONS

European Search Report for EP Application No. 09004664, dated Sep. 8, 2009.

(Continued)

*Primary Examiner* — Emily Schmidt
*Assistant Examiner* — Lauren M Peng
(74) *Attorney, Agent, or Firm* — McDonnell Boehnen Hulbert & Berghoff LLP

(57) ABSTRACT

The body of a portable drug delivery device, especially an injection pen, is provided on its outer surface with a recess, in which directly accessible information is displayed. The information is protected against damages during everyday use by the recessed location.

1 Claim, 2 Drawing Sheets

(56) References Cited

U.S. PATENT DOCUMENTS

| | | | |
|---|---|---|---|
| 2001/0028308 A1* | 10/2001 | De La Huerga | A61M 5/14212 340/573.1 |
| 2004/0010233 A1 | 1/2004 | Hjertman et al. | |
| 2004/0089292 A1* | 5/2004 | Pollet | A61M 15/0025 128/200.23 |
| 2007/0255204 A1* | 11/2007 | McLean | A61C 5/062 604/90 |
| 2008/0017188 A1* | 1/2008 | Pardonge | A61M 15/009 128/200.14 |

OTHER PUBLICATIONS

International Search Report for PCT Application No. PCT/EP2010/054341, dated Jun. 23, 2010.
International Preliminary Report on Patentability for International App. No. PCT/EP2010/054341, dated Oct. 4, 2011.

* cited by examiner

DRUG DELIVERY DEVICE BODY

CROSS REFERENCE TO RELATED APPLICATIONS

The present application is a U.S. National Phase Application pursuant to 35 U.S.C. §371 of International Application No. PCT/EP2010/054341 filed Mar. 31, 2010, which claims priority to European Patent Application No. 09004664.0 filed on Mar. 31, 2009 and U.S. Provisional Patent Application No. 61/169,846. The entire disclosure contents of these applications are herewith incorporated by reference into the present application.

FIELD OF INVENTION

The present invention relates to a body or housing of a portable drug delivery device, especially a pen-type drug delivery device or injection pen.

BACKGROUND

Portable drug delivery devices are generally known for the administration of a medicinal substance or fluid, for example insulin, growth hormones or other drugs, being suitable for self-administration by a patient. A drug delivery device is especially useful in the shape of a pen, which can be handled easily and kept everywhere available. A sophisticated type of drug delivery device is constructed to be refillable and reusable many times. To secure a long life of the device, it is important to avoid damages caused during everyday use.

Some drug delivery devices are constructed to deliver a plurality of different doses. One particular example of such a drug delivery device is described in EP 1 923 083 A1. The drug delivery device shown therein allows a user to activate the delivery device. For that purpose, the drug delivery device includes a drive mechanism suitable for use in pen-type injectors, where an amount of pre-set doses of medicinal product can be administered. A needle unit can be attached to the drug delivery device for dispensing the medicinal product into a patient's body.

Necessary information about the drug delivery or the dosage should be directly accessible by the user of the device and should therefore preferably be connected to the body of the device.

SUMMARY

It is an object of the present invention to provide a portable drug delivery device with directly accessible information by means that are least possibly prone to damage or malfunction.

This object is achieved with the drug delivery device body according to claim 1. Embodiments derive from the dependent claims.

The drug delivery device body comprises an outer surface and a recess in the outer surface. The recess is provided for the display of a piece of information.

The recess can be shallow and is preferably located at a position on the outer surface of the body where a written or printed information is easily readable. The information is to be displayed on the outer surface of the body within the recess. The information can be applied by printing or by molding or forming a surface structure in relief, for example. The drug delivery device body may further comprise a label located within the recess. A printed or structured label carrying the information can be used advantageously in view of cost-effective production. If the recess is provided for a label, the depth of the recess is preferably adapted to the thickness of the label. The label can be fastened on the body surface within the recess by means of an adhesive, especially by means of an adhesive layer that is readily provided on the back of the label in advance, so that the label can be fastened immediately without use of further means or tools. This allows a particularly easy manufacturing of the body of a device comprising the necessary direct information.

If the thickness of the relief structure or the label is less than or at most equal to the depth of the recess, the level of the most elevated surfaces of the relief structure or the level of the outer surface of the label, respectively, will not exceed the level of the outer surface of the device body. The information placed in the recess is thus protected from being scratched or damaged during usage or storing of the drug delivery device, and particularly a label is protected from peeling. Furthermore, sliding, gliding or rolling of the drug delivery device on a plane surface will not scratch or damage the surface of the label or of the printed or molded information, nor even cause abrasion or scratches that might render the information illegible.

In an embodiment of the drug delivery device body, it is intended for a pen-type device of elongated shape, provided at one end with an operation button, and the recess is located near the end of the body where the operation button is to be placed.

In another embodiment, the recess is provided with an optically transparent cover protecting the printed or molded information or label. The cover can be a thin foil, for example. The cover is preferably formed of an essentially scratch-resistant transparent material and may be transparent plastic or glass. The cover prevents or at least reduces damage due to gliding or scraping of the drug delivery device on a surface that is not completely flat, especially on a rough surface.

In another embodiment, the body is part of an assembled drug delivery device, especially an injection pen.

The term "drug" as used herein preferably means a pharmaceutical formulation containing at least one pharmaceutically active compound having a molecular weight up to 1500 Da, or a pharmaceutically active peptide, protein, DNA, RNA, antibody, enzyme, hormone or oligonucleotide, or a mixture thereof, preferably comprising at least one peptide, further preferred a peptide for the treatment of diabetes mellitus or complications associated with diabetes mellitus such as diabetic retinopathy, especially preferred human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N- palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 preferably means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative; or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)$_5$-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)$_5$-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)$_5$-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)$_5$-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)$_5$ des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)$_5$-des Pro36, Pro37, Pro38 [Met(O)14, Trp(O2) 25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)$_5$-des Pro36, Pro37, Pro38 [Met(O)14, Trp(O2) 25, Asp28] Exendin-4(1-39)-(Lys)6-NH2;
or a pharmaceutically acceptable salt or solvat of any one of the afore-mentioned Exedin-4 derivatives.

Hormones are preferably hypophysis hormones or hypothalamus hormones or regulatory active peptides and their antagonists as listed in Rote Liste, ed. 2008, Chapter 50. Examples of hormones are Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. Ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Other features of examples and embodiments of the invention will become apparent from the following detailed description taken in conjunction with the accompanying drawings.

DETAILED DESCRIPTION

The figures show additional features that are not essential for the invention and are represented by way of illustration only. The figures are not drawn to scale.

Figure 1:
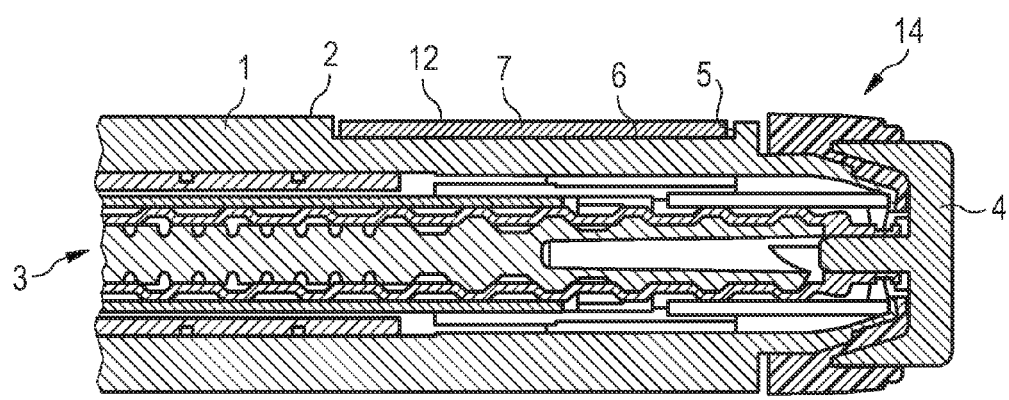
FIG. 1 shows a part of a cross-section of an embodiment of a pen-type drug delivery device having a body according to the invention.

FIG. 1 shows a part of a cross-section of an embodiment of a pen-type drug delivery device or injection pen 14 comprising a body 1 or housing with an outer surface 2. On a side of the body 1 that is opposite to the outer surface 2, an inner volume of the body 1 is occupied by a mechanism 3, which is provided for the operation of the device, especially for delivering a prescribed dose of a drug. The mechanism 3 can be operated by pressing or rotating an operation button 4, which is located at an end of the body 1, for example. A recess 5 is formed in the outer surface of the body 1. The recess 5 is provided to carry the information and has a surface 6 on a level that is inferior with respect to the level of the outer surface 2 of the body outside the recess 5. The recess 5 is preferably shallow and can be located in the vicinity of the operation button 4 or near the end of the device where the operation button 4 is located, for example. The information can be applied directly to the surface 6 of the recess 5, for example by printing or molding. In the embodiment according to FIG. 1 the surface 6 of the recess 5 bears a label 7. The label 7 carries the information on its outer surface 12. The cross-section of FIG. 1 shows a preferred embodiment, in which the label 7 does not exceed or rise above the level of the outer surface 2 of the body 1 as present outside the recess 5.

Figure 2:
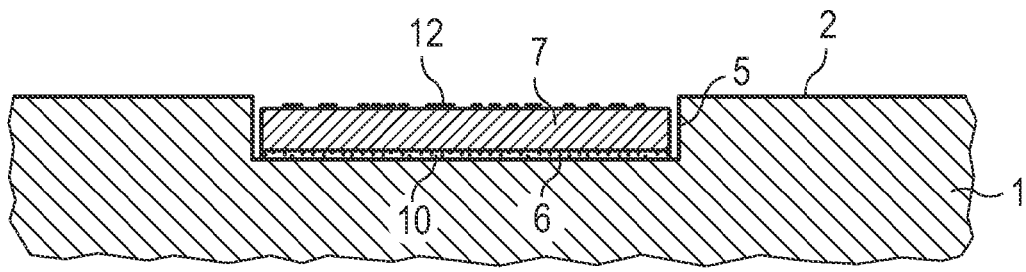
FIG. 2 shows a cross-section of the recess bearing a label.

FIG. 2 shows a cross-section of the body 1 at the location of the recess 5 according to the embodiment of FIG. 1. The label 7 in the recess 5 carries the information on its outer surface 12 in printed or molded form. The label 7 can be fastened to the surface 6 of the recess 5 by means of an adhesive layer 10, for example.

Figure 3:
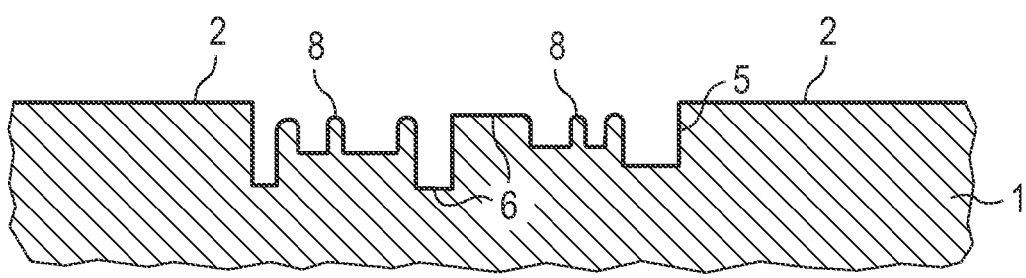
FIG. 3 shows a cross-section of the recess bearing a relief structure.

FIG. 3 shows a cross-section of the recess 5 bearing a relief structure 8. This is a further example of how immediately available information can be placed on the body surface within the recess 5. The relief structure 8 can be formed directly in the surface 6 of the recess 5, so that it forms an integral part of the body 1, which can be produced from plastic material, for example. Instead, a structured label or molded element can be applied to the body 1 in the recess 5. The cross-section of FIG. 3 shows a preferred embodiment, in which the relief structure 8 does not exceed or rise above the level of the outer surface 2 of the body 1 as present outside the recess 5. Additionally, the relief structure 8 can be protected with a cover similar to the one shown in FIG. 4.

Figure 4:
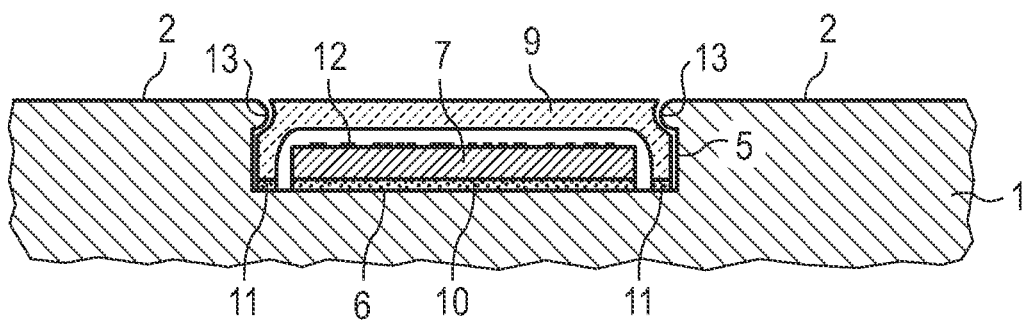
FIG. 4 shows a cross-section of the recess bearing a label and a cover.

FIG. 4 shows a cross-section of the recess 5 bearing a label 7 and a cover 9. The label 7 carries the information on its outer surface 12 in printed or molded form. The label 7 is preferably fastened to the outer surface 6 of the recess 5 by means of an adhesive layer 10. The cover 9 is not necessary and can be left off, according to the embodiment shown in FIG. 2. On the other hand, the adhesive layer 10 is not necessary to fasten the label 7, if the label 7 is held in place by the cover 9 and the cover 9 is fastened to the body 1. In the embodiment of FIG. 4 the cover 9 is fastened by means of the further adhesive layer 11, but it could also be applied by fastening means like hooks, spikes or protruding rims 13. The cross-section of FIG. 4 shows a preferred embodiment, in which the cover 9 does not exceed or rise above the level of the outer surface 2 of the body 1 as present outside the recess 5.

The label 7 may cover essentially all of the surface 6 of the recess 5 as in the embodiment according to FIG. 2, or the label 7 may be restricted to a smaller area of the surface 6 of the recess 5 as shown in FIG. 4.

Embodiments in which the information is directly printed or molded onto the surface 6 of the recess 5 without using a label or other separate element can also be provided with a cover according to the one shown in FIG. 4, in order to have an even better protection of the information against damages.

Although the present invention and its advantages have been described in detail, it should be understood that various changes, substitutions and alterations can be made herein without departing from the spirit and scope of the invention as defined by the appended claims. Also features described in conjunction with various embodiments can be combined in different ways without leaving the scope of the invention.

The invention claimed is:

1. A drug delivery device body, comprising:
   a body material;
   an outer surface of the body material having a defined level and forming part of a pen-type drug delivery device or injection pen;
   a mechanism located in an inner volume of the body on a side of the body that is opposite to the outer surface, where the mechanism is configured to set and deliver through injection a plurality of doses of a drug;
   a recess formed in the body material of the outer surface, the recess having a surface below the level of the outer surface;
   a label located within the recess, the label applied to the surface of the recess and does not exceed the level of the outer surface of the outer surface; and
   a transparent cover that covers the recess and does not exceed the level of the outer surface of the outer body.

* * * * *